United States Patent
Fichert et al.

(10) Patent No.: US 9,066,970 B2
(45) Date of Patent: Jun. 30, 2015

(54) PHARMACEUTICAL COMPOSITIONS CONTAINING SUBSTITUTED 6-DEOXY-6-SULFANYLCYCLODEXTRIN

(75) Inventors: Thomas Fichert, Warendorf (DE); Johannes Gerber, Mainz (DE); Ingo Bichlmaier, Helsinki (FI)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 0 days.

(21) Appl. No.: 13/635,287

(22) PCT Filed: Mar. 18, 2011

(86) PCT No.: PCT/EP2011/001356
§ 371 (c)(1),
(2), (4) Date: Sep. 14, 2012

(87) PCT Pub. No.: WO2011/116909
PCT Pub. Date: Sep. 29, 2011

(65) Prior Publication Data
US 2013/0005834 A1    Jan. 3, 2013

(30) Foreign Application Priority Data
Mar. 22, 2010    (DE) .................. 10 2010 012 281

(51) Int. Cl.
*A61K 31/724*    (2006.01)

(52) U.S. Cl.
CPC ................................. *A61K 31/724* (2013.01)

(58) Field of Classification Search
CPC .................................................. A61K 31/724
See application file for complete search history.

(56) References Cited

U.S. PATENT DOCUMENTS

| 4,889,634 A | 12/1989 | El-Rashidy | |
| 5,296,472 A * | 3/1994 | Sanchez et al. | 514/58 |
| 2009/0239819 A1 | 9/2009 | Wang et al. | |
| 2009/0312724 A1 | 12/2009 | Pipkin et al. | |

FOREIGN PATENT DOCUMENTS

| JP | 8071146 | 3/1996 |
| WO | WO 01/40316 | 6/2001 |
| WO | WO 02/36105 | 5/2002 |
| WO | WO 2005/042584 | 5/2005 |
| WO | WO 2006/001844 | 1/2006 |

OTHER PUBLICATIONS

Hans H. Baer et al. "Heptakis [6-S-(2,3-dihydroxypropyl)-6-thio] cyclomaltoheptaose and its sulfone: water soluble β-cyclodextrin derivatives having modified polarity" Carbohydrate Research, vol. 280, No. 2, Jan. 11, 1996, p. 315-321.

Erika A. Zannou et al. "Osmotic Properties of Sulfobutylether and Hydroxypropyl Cyclodextrins" Pharmaceutica Research, vol. 18, No. 8, 2001, pp. 1226-1231.

Julia M. Adam Cyclodextrin-Derived Host Molecules as Reversal Agents for the Neuromuscular Blocker Rocuronium Bromide: Synthesis and Structure-Activity Relationships, J. Med. Chem, vol. 45, 2002, pp. 1806-1816.

* cited by examiner

*Primary Examiner* — Wu-Cheng Winston Shen
*Assistant Examiner* — Christopher R Stone
(74) *Attorney, Agent, or Firm* — Jacobson Holman, PLLC.

(57) ABSTRACT

The present invention relates to pharmaceutical compositions containing substituted 6-deoxy-6-sulfanylcyclodextrins as well as their use as osmotic agents, in particular for use in dialysis therapy.

5 Claims, 1 Drawing Sheet

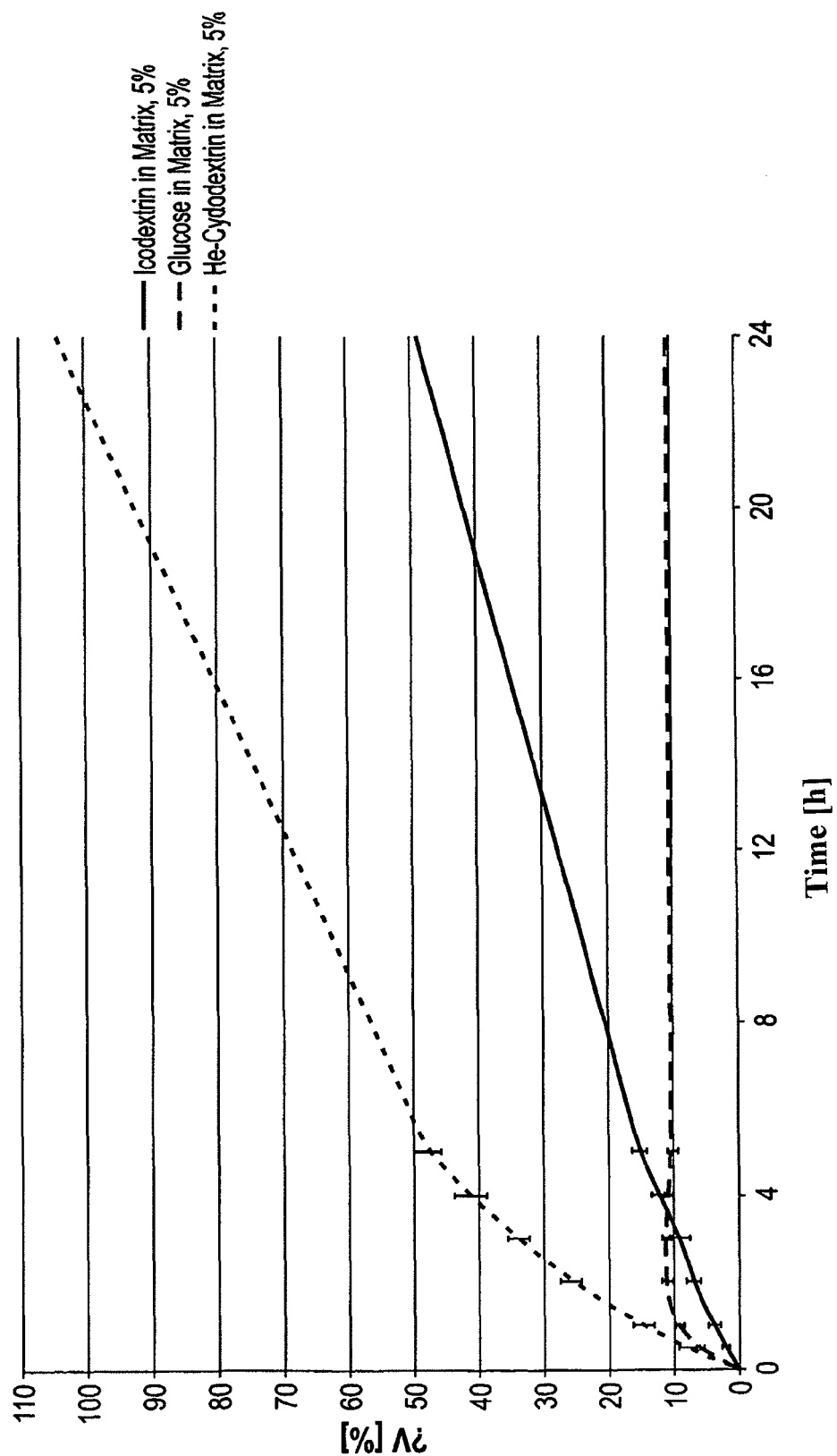

PHARMACEUTICAL COMPOSITIONS CONTAINING SUBSTITUTED 6-DEOXY-6-SULFANYLCYCLODEXTRIN

This is a national stage of PCT/EP11/001,356, filed Mar. 18, 2011 and published in German, which claims priority from German Application No. 10 2010 012 281.5, filed Mar. 22, 2010, each of which is hereby incorporated by reference in its entirety.

The present invention relates to pharmaceutical compositions containing substituted 6-deoxy-6-sulfanylcyclodextrins, as well as their use as osmotics, in particular for use in dialysis therapy.

BACKGROUND OF THE INVENTION

Omotically active compounds (osmotics) are used widely in pharmacy and medicine. For example, osmotics are used to adjust the tonicity of drugs, in particular parenteral medications, where the osmotic pressure of a drug is adjusted to be hypotonic, hypertonic or isotonic, depending on how it is administered. For example, the osmotic pressure of a parenteral drug solution may be adjusted to match the osmotic pressure of human blood by adding an osmotic agent (isosmotic solutions).

Furthermore, osmotics are used in dialysis therapy, in particular in peritoneal dialysis, to withdraw excess water from the dialysis patient.

The peritoneal dialysis method is based on the fact that a solution containing osmotically active compounds is introduced into the abdominal cavity of a dialysis patient through a catheter. The solution is left in the patient's abdominal cavity, where it manifests its osmotic effect for a certain period of time (usually a few hours). In other words, endogenous water is withdrawn from the patient into the abdominal cavity. After a certain dwell time, the peritoneal dialysis solution, which is then dilute, is drained out through a catheter.

This principle is employed in various methods of peritoneal dialysis therapy. For example, the methods of intermittent peritoneal dialysis (IPD), nocturnal intermittent peritoneal dialysis (NIPD), continuous cyclic peritoneal dialysis (CCPD) or continuous ambulant peritoneal dialysis (CAPD) may be employed as needed. In IPD, NIPD and CCPD, instruments which support the patient in performing the peritoneal dialysis method are used. CAPD is a manual method.

By adding osmotically active compounds, it should be ensured in particular that the osmotic pressure of the peritoneal dialysis solution is high enough during the entire dwell time in the abdominal cavity to withdraw water from the patient. In other words, water goes from the patient's circulation into the abdominal cavity (ultrafiltration).

However, because of the transfer of water into the abdominal cavity, dilution of the peritoneal dialysis solution introduced there necessarily occurs. As a result of this dilution, there is a decline in the concentration of the osmotically active compound and thus also the osmotic pressure of this solution.

If the osmotic pressure of the peritoneal dialysis solution drops because of this dilution, this in turn results in a decrease in or even a complete standstill of the transfer of water into the abdominal cavity per unit of time. In these cases, there is no longer an effective withdrawal of water with advancing dwell time of the peritoneal dialysis solution in the patient's abdominal cavity.

Through absorption of osmotically active compounds into the patient's bloodstream, the direction of the transfer of water may even be reversed, i.e., water goes from the abdominal cavity into the patient's bloodstream (negative ultrafiltration). This is the case when the dilute peritoneal dialysis solution in the abdominal cavity has a lower osmotic pressure than the patient's endogenous water (e.g., blood).

By adding suitable osmotically active compounds to the peritoneal dialysis solution, the osmotic pressure may be maintained for a treatment time, which is suitable for peritoneal dialysis, so that there is no excessive decline in ultrafiltration within the dwell time of the solution in the abdominal cavity. A negative ultrafiltration is thus also largely prevented.

The solutions used in the peritoneal dialysis therapy usually contain sugar monomers or polymers, for example, glucose or polyglucose (e.g., starch derivatives) as osmotically active compounds.

U.S. Pat. No. 4,889,634 relates to a peritoneal dialysis solution containing hydroxypropyl-β-cyclodextrin.

JP 8071146 relates to a peritoneal dialysis solution containing α- or γ-cyclodextrin, 2-hydroxyethyl ether, 2-hydroxypropyl ether, 6-O-α-glucosyl or 6-O-α-maltosyl derivatives of α-, β- and γ-cyclodextrin.

However, the state of the art describes cyclodextrin compounds which are not selectively substituted. Instead these cyclodextrin derivatives are mixtures of a wide variety of compounds (different degrees of substitution, different positional isomers) because the substitution of cyclodextrins takes place selectively on certain hydroxyl groups of the cyclodextrins only to a very limited extent.

SUMMARY OF THE INVENTION

One object of the present invention is to make available cyclodextrin derivatives for pharmaceutical compositions, which have a more uniform substitution pattern in comparison with the state-of-the-art cyclodextrin derivatives, i.e., for example, the presence of different positional isomers is reduced and/or ruled out.

Another object of the present invention is to make available cyclodextrin derivatives, which have a high water solubility, an improved osmotic activity and an increased ultrafiltration in comparison with the state-of-the-art cyclodextrins and which are thus suitable for pharmaceutical compositions for dialysis therapy in particular.

This objective is achieved by the subject of the patent claims.

BRIEF DESCRIPTION OF THE DRAWINGS

FIG. 1 is a graph showing the osmotic effect of various compounds.

DETAILED DESCRIPTION OF THE INVENTION

The inventive 6-deoxy-6-sulfanylcyclodextrins are characterized by a more uniform substitution pattern in comparison with the state-of-the-art cyclodextrin derivatives, i.e., their structure is defined more precisely (for example, lower proportion of different positional isomers; uniform degree of substitution).

As a result, adverse effects based on the presence of a wide variety of different substitution patterns can be largely ruled out. This increases patient safety.

In particular the efficacy of the inventive 6-deoxy-6-sulfanylcyclodextrins can be attributed to defined compounds and is not based on the effects of a complex mixture of different cyclodextrin derivatives. This also increases patient safety and facilitates the evaluation of pharmacological and/or clinical data in particular.

Furthermore, mixtures of substituted cyclodextrins having a composition that is reproducible only to a limited extent may lead to a lack of reproducibility in determination of experimental data, e.g., in performing pharmacological or toxicological in vivo or ex vivo experiments, for example, as well in conducting clinical studies.

A first subject matter of this invention relates to 6-deoxy-6-sulfanylcyclodextrins of the general structure I:

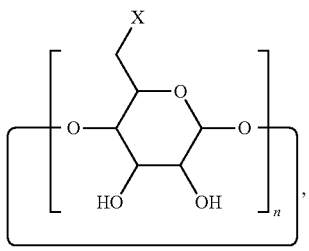

where
a) X stands for S—R or OH,
b) n stands for 6, 7 or 8,
c) the degree of substitution, based on the S—R radical, is ≥0.0001 and ≤n, and
d) R is selected from the group consisting of $C_{1-6}$-alkyl-$R^1R^2$, —$C_{1-6}$-alkyl-$N^+R^3R^4R^{5.}$ $C_{1-6}$-alkyl-COOH, C(=O)$C_{1-6}$-alkyl-COOH, —C(=O)—$CH_2$—C(OH)(COOH)—$CH_2$—COOH, dihydroxylated $C_{1-6}$-alkyl, $C_{1-6}$-alkyl-$PO_3H_2$ and —$C_{1-6}$-alkyl-$SO_3H$, where $R^1$, $R^2$, $R^3$, $R^4$ and $R^5$, independently of one another, stand for —H or —$C_{1-3}$-alkyl, for use as an osmotic agent.

A preferred subject matter of this invention relates to 6-deoxy-6-sulfanylcyclodextrins of the general structure II:

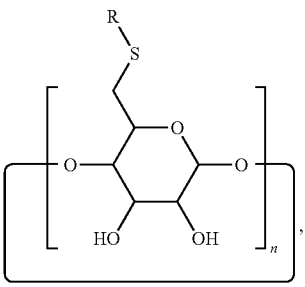

where
a) n stands for 6, 7 or 8, and
b) R is selected from the group consisting of —$C_{1-6}$-alkyl-$NR^1R^2$, —$C_{1-6}$-alkyl-$N^+R^3R^4R^{5.}$ —$C_{1-6}$-alkyl-COOH, —C(=O)$C_{1-6}$-alkyl-COOH, —C(=O)—$CH_2$—C(OH)(COOH)—$CH_2$—COOH, dihydroxylated $C_{1-6}$-alkyl, $C_{1-6}$-alkyl-$PO_3H_2$ and —$C_{1-6}$-alkyl-$SO_3H$, where $R^1$, $R^2$, $R^3$, $R^4$ and $R^5$, independently of one another, stand for —H or —$C_{1-3}$-alkyl, for use as osmotic agents.

In the sense of the present invention, the term "$C_{1-6}$-alkyl" comprises saturated or unsaturated hydrocarbon radicals, which may be branched or linear and may contain 1, 2, 3, 4, 5 or 6 carbon atoms. Preferably $C_{1-6}$-alkyl comprises the radicals $C_{1-6}$-alkanyl, $C_{2-6}$-alkenyl and $C_{2-6}$-alkynyl, where $C_{2-6}$-alkenyls have at least one C—C double bond, and $C_{2-6}$-alkynyls have at least one C—C-triple bond, whereas $C_{1-6}$-alkanyls are completely saturated. Preferably $C_{1-6}$-alkyl is selected from the group comprising methyl, ethyl, isopropyl, n-propyl, isobutyl, n-butyl, sec-butyl, tert-butyl, n-pentyl, isopentyl, neo-pentyl, isohexyl, n-hexyl, neo-hexyl, 3-methylpentyl, 2,3-dimethylbutyl, ethenyl, ethynyl, prop-1-enyl, isobutenyl, n-butenyl, cis-2-butenyl, trans-2-butenyl, 1,2-butadienyl, 1,3-butadienyl, pent-1-enyl, cis-pent-2-enyl, trans-pent-2-enyl, 2-methylbut-1-enyl, 2-methyl-but-2-enyl, 3-methyl-but-1-enyl, hex-1-enyl, hex-2-enyl and hex-3-enyl.

In the sense of the present invention, the term "$C_{1-3}$-alkyl" comprises acyclic, saturated or unsaturated hydrocarbon radicals, which may be branched or linear and may contain 1, 2 or 3 carbon atoms. Preferably $C_{1-3}$-alkyl comprises the radicals $C_{1-3}$-alkanyl, $C_{2-3}$-alkenyl and $C_{2-3}$-alkynyl, where $C_{2-3}$-alkenyls have at least one C—C double bond and $C_{2-3}$-alkynyls have at least one C—C-triple bond, whereas $C_{1-3}$-alkanyls are completely saturated. Preferably $C_{1-3}$-alkyl is selected from the group comprising methyl, ethyl, isopropyl, n-propyl, ethenyl, ethynyl and prop-1-enyl.

The basic —$C_{1-6}$-alkyl-$NR^1R^2$ radical may be protonated, i.e., may be in cationic form and may be present in the form of a salt with anions—for example, fluoride, chloride, bromide, iodide, bicarbonate, carbonate, dihydrogen phosphate, hydrogen phosphate, phosphate, lactate, pyruvate.

The $NR^1R^2$ group may be bound to any possible site on the —$C_{1-6}$-alkyl.

In a preferred embodiment, the $C_{1-6}$-alkyl-$NR^1R^2$ radical is selected from the group comprising $C_{1-6}$-alkyl-N(methyl)$_2$, $C_{1-6}$-alkyl-N(ethyl)$_2$, $C_{1-6}$-alkyl-N(propyl)$_2$ and $C_{1-6}$-alkyl-N(isopropyl)$_2$.

In another preferred embodiment, the $C_{1-6}$-alkyl-$NR^1R^2$ radical is selected from the group comprising $CH_2$—N(methyl)$_2$, $CH_2$—N(ethyl)$_2$, $CH_2$—N(propyl)$_2$, $CH_2$—N(isopropyl)$_2$, $(CH_2)_2$—N(methyl)$_2$, $(CH_2)_2$—N(ethyl)$_2$, $(CH_2)_2$—N(propyl)$_2$, $(CH_2)_2$—N(isopropyl)$_2$, $(CH_2)_3$—N(methyl)$_2$, $(CH_2)_3$—N(ethyl)$_2$, $(CH_2)_3$—N(propyl)$_2$, $(CH_2)_3$—N(isopropyl)$_2$, $(CH_2)_4$—N(methyl)$_2$, $(CH_2)_4$—N(ethyl)$_2$, $(CH_2)_4$—N(propyl)$_2$, $(CH_2)_4$—N(isopropyl)$_2$, $(CH_2)_5$—N(methyl)$_2$, $(CH_2)_5$—N(ethyl)$_2$, $(CH_2)_6$—N(propyl)$_2$, $(CH_2)_5$—N(isopropyl)$_2$, $(CH_2)_6$—N(methyl)$_2$, $(CH_2)_4$—N(ethyl)$_6$, $(CH_2)_4$—N(propyl)$_6$ and $(CH_2)_6$—N(isopropyl)$_2$.

The $C_{1-6}$-alkyl-$N^+R^3R^4R^5$ radical may be present as a salt with anions—for example, fluoride, chloride, bromide, iodide, bicarbonate, carbonate, dihydrogen phosphate, hydrogen phosphate, phosphate, lactate, pyruvate.

The —$N^+R^3R^4R^5$ group may be bound to any possible site on the —$C_{1-5}$-alkyl.

The $C_{1-6}$-alkyl-$N^+R^3R^4R^5$ radical is preferably selected from the group comprising $CH_2$-alkyl-$N^+$(methyl)$_3$, $CH_2$-alkyl-$N^+$(ethyl)$_3$, $CH_2$-alkyl-$N^+$(propyl)$_3$, $CH_2$-alkyl-$N^+$(isopropyl)$_3$, $(CH_2)_2$-alkyl-$N^+$(methyl)$_3$, $(CH_2)_2$-alkyl-$N^+$(ethyl)$_3$, $(CH_2)_2$-alkyl-$N^+$(propyl)$_3$, $(CH_2)_2$-alkyl-$N^+$(isopropyl)$_3$, $(CH_2)_3$-alkyl-$N^+$(methyl)$_3$, $(CH_2)_3$-alkyl-$N^+$(ethyl)$_3$, $(CH_2)_3$-alkyl-$N^+$(propyl)$_3$, $(CH_2)_3$-alkyl-$N^+$(isopropyl)$_3$, $(CH_2)_4$-alkyl-$N^+$(methyl)$_3$, $(CH_2)_4$-alkyl-$N^+$(ethyl)$_3$, $(CH_2)_4$-alkyl-$N^+$(propyl)$_3$, $(CH_2)_4$-alkyl-$N^+$(isopropyl)$_3$, $(CH_2)_5$-alkyl-$N^+$(methyl)$_3$, $(CH_2)_5$-alkyl-$N^+$(ethyl)$_3$, $(CH_2)_5$-alkyl-$N^+$(propyl)$_3$ and $(CH_2)_5$-alkyl-$N^+$(isopropyl)$_3$.

The acid radicals $C_{1-6}$-alkyl-COOH, C(=O)$C_{1-6}$-alkyl-COOH, —C(=O)—$CH_2$—C(OH)—(COOH)—$CH_2$—COOH (citric acid radical), $C_{1-6}$-alkyl-$PO_3H_2$ and $C_{1-6}$-alkyl-$SO_3H$ may be deprotonated, i.e., they may be present in anionic form and may be present as a salt with cations—for example, sodium, potassium, potassium, magnesium, calcium, ammonium.

The radicals —COOH, —PO$_3$H$_2$ and SO$_3$H may be bound to any possible site on the C$_{1-6}$-alkyl.

In a preferred embodiment, the C$_{1-6}$-alkyl-COOH radical is selected from the group comprising CH$_2$—COOH, (CH$_2$)$_2$—COOH, (CH$_2$)$_3$—COOH, (CH$_2$)$_4$—COOH, (CH$_2$)$_5$—COOH and (CH$_2$)$_6$—COOH.

The C(=O)C$_{1-6}$-alkyl-COOH radical is preferably selected from the group comprising C(=O)CH$_2$—COOH, C(=O)(CH$_2$)$_2$—COOH, C(=O)(CH$_2$)$_3$—COOH, C(=O)(CH$_2$)$_4$—COOH, C(=O)(CH$_2$)$_5$—COOH and C(=O)(CH$_2$)$_6$—COOH.

In a preferred embodiment, the C$_{1-6}$-alkyl-PO$_3$H$_2$ radical is selected from the group comprising CH$_2$—PO$_3$H$_2$, (CH$_2$)$_2$—PO$_3$H$_2$, (CH$_2$)$_3$—PO$_3$H$_2$, (CH$_2$)$_4$—PO$_3$H$_2$, (CH$_2$)$_5$—PO$_3$H$_2$, —(CH$_2$)$_6$—PO$_3$H$_2$, —CH=CH—PO$_3$H$_2$, —CH$_2$—CH=CH—PO$_3$H$_2$, —(CH$_2$)$_2$—CH=CH—PO$_3$H$_2$, —(CH$_2$)$_3$—CH=CH—PO$_3$H$_2$ and —(CH$_2$)$_4$—CH=CH—PO$_3$H$_2$.

The C$_{1-6}$-alkyl-SO$_3$H radical is preferably selected from the group comprising CH$_2$—SO$_3$H, (CH$_2$)$_2$—SO$_3$H, (CH$_2$)$_3$—SO$_3$H, (CH$_2$)$_4$—SO$_3$H, (CH$_2$)$_5$—SO$_3$H and (CH$_2$)$_6$—SO$_3$H.

In the sense of this description, the term "degree of substitution" stands for the average number of moles of radical R based on 1 mol cyclodextrin.

In a preferred embodiment, the degree of substitution of the inventive 6-deoxy-6-sulfanylcyclodextrin is $\geq n-1$ and $\leq n$.

In another preferred embodiment, the degree of substitution of the inventive 6-deoxy-6-sulfanylcyclodextrin is $\geq n-1$ and $\geq n$.

For the case when n stands for 6, the degree of substitution may assume values from >0 to at most 6 (this corresponds to six substituents per 6-deoxy-6-sulfanyl-α-cyclodextrin molecule).

For the case when n stands for 7, the degree of substitution may assume values from >0 to at most 7 (this corresponds to seven substituents per 6-deoxy-6-sulfanyl-β-cyclodextrin molecule).

For the case when n stands for 8, the degree of substitution may assume values from >0 to at most 8 (this corresponds to eight substituents per 6-deoxy-6-sulfanylcyclodextrin molecule).

For the case when n=6, the degree of substitution preferably has a value of 1 to 6 or 2 to 6, more preferably 3 to 6, even more preferably 4 to 6, most preferably 5 to 6 or 5.5 to 6 and in particular 6.

For the case when n=7, the degree of substitution preferably has a value of 1 to 7 or 2 to 7, more preferably 3 to 6 or 4 to 7, even more preferably 5 to 7, most preferably 6 to 7 or 6, 5 to 7 and in particular 7.

For the case when n=8, the degree of substitution preferably has a value of 1 to 8 or 2 to 8, more preferably 3 to 8 or 4 to 8, even more preferably 5 to 8 or 6 to 8, most preferably 7 to 8 or 7.5 to 8 and in particular 8.

A 7.5 wt % aqueous solution of the inventive 6-deoxy-6-sulfanylcyclodextrin preferably has a theoretical osmolarity of $\geq 5$ mosm/L, more preferably greater than mosm/L, even more preferably greater than $\geq 10$ mosm/L, most preferably greater than $\geq 12.5$ mosm/L and in particular greater than $\geq 15$ mosm/L.

For the purposes of this description, the term "theoretical osmolarity" stands for theoretically calculated osmolarity. The person skilled in the art will be familiar with methods of calculating this value.

In a preferred embodiment, the colloid osmotic pressure of a 7.5 wt % solution of the inventive 6-deoxy-6-sulfanylcyclodextrin is $\geq 50$ mosm/L or $\geq 60$ mosm/L, more preferably $\geq 70$ mosm/L or 80 mosm/L, even more preferably $\geq 90$ mosm/L or 100 mosm/L, most preferably 110 mosm/L or 120 mosm/L and in particular 130 mosm/L or $\geq 140$ mosm/L.

In another preferred embodiment, the colloid osmotic pressure of a 7.5 wt % solution of the inventive 6-deoxy-6-sulfanylcyclodextrin is $\geq 150$ mosm/L or $\geq 160$ mosm/L, more preferably $\geq 170$ mosm/L or $\geq 180$ mosm/L, even more preferably $\geq 190$ mosm/L or $\geq 200$ mosm/L, most preferably $\geq 210$ mosm/L or $\geq 220$ mosm/L and in particular $\geq 230$ mosm/L or $\geq 240$ mosm/L.

In another preferred embodiment, the colloid osmotic pressure of a 7.5 wt % solution of the inventive 6-deoxy-6-sulfanylcyclodextrin is 50 to 500 mosm/L, more preferably 75 mosm/L to 400 mosm/L, even more preferably 100 to 300 mosm/L, most preferably 110 mosm/L to 275 mosm/L and in particular 120 mosm/L to 250 mosm/L.

In another preferred embodiment, the colloid osmotic pressure of a 7.5 wt % solution of the inventive 6-deoxy-6-sulfanylcyclodextrin is 100 to 500 mosm/L, more preferably 100 mosm/L to 400 mosm/L, even more preferably 100 to 350 mosm/L, most preferably 100 mosm/L to 325 mosm/L and in particular 100 mosm/L to 290 mosm/L.

For the purposes of this description, the term "colloid osmotic pressure" stands for the experimentally measured osmotic pressure of the solution, which is composed of the osmotic pressure and the oncotic pressure. The person skilled in the art will be familiar with suitable methods for determining this value.

The osmolality of a 7.5 wt % aqueous solution of the inventive 6-deoxy-6-sulfanylcyclodextrin is preferably >5 mosm/kg, more preferably $\geq 27.5$ mosm/kg, even more preferably $\geq 10$ mosm/kg, most preferably $\geq 12$ mosm/kg and in particular $\geq 15$ mosm/kg.

For the purposes of this description, the term "osmolality" stands for the osmolality the solution determined experimentally by freezing point reduction. The person skilled in the art is familiar with methods of freezing point reduction.

The osmolarity of a 7.5 wt % aqueous solution of the inventive 6-deoxy-6-sulfanylcyclodextrin, determined experimentally by a reduction in freezing point, is preferably $\geq 15$ mosm/L, more preferably $\geq 17$ mosm/L, even more preferably $\geq 19$ mosm/L, most preferably $\geq 21$ mosm/L and in particular $\geq 23$ mosm/L.

The inventive 6-deoxy-6-sulfanylcyclodextrin is preferably suitable as an osmotic agent for adjusting the tonicity of drugs, in particular pharmaceutical solutions for parenteral administration.

In a preferred embodiment, the inventive 6-deoxy-6-sulfanylcyclodextrin is used in dialysis therapy, preferably in hemodialysis and/or peritoneal dialysis therapy.

The inventive 6-deoxy-6-sulfanylcyclodextrin is suitable for use in peritoneal dialysis therapy in particular.

Another subject matter of this invention relates to dialysis solutions containing at least one inventive 6-deoxy-6-sulfanylcyclodextrin.

In a preferred embodiment, the inventive dialysis solution is a hemodialysis solution or a peritoneal dialysis solution. The inventive dialysis solution is a peritoneal dialysis solution in particular.

Dosage forms used in dialysis therapy are preferably concentrates in multicomponent systems or ready-to-use dialysis solutions.

For the purposes of this invention, the term "dialysis solution" refers to a ready-to-use dosage form for dialysis therapy, i.e., a liquid preparation which is suitable for administration as such. In particular the dialysis solution need not be diluted and/or mixed with other preparations prior to administration.

In contrast with the dialysis solutions described above, concentrates which may be in either liquid, semisolid or solid form, are diluted with water or aqueous solutions or are dissolved in water or aqueous solutions before being administered. Similarly, the components of a multicomponent system are mixed together before administered to yield a ready-to-use dialysis solution. Concentrates and multicomponent systems may thus be regarded as precursors of the inventive dialysis solution.

The inventive dialysis solution is preferably a hemodialysis solution or a peritoneal dialysis solution. Hemodialysis and peritoneal dialysis solutions usually contain electrolytes in a concentration which corresponds essentially to the plasma electrolyte concentration. The electrolytes usually comprise sodium, potassium, calcium, magnesium and chloride ions.

Dialysis solutions usually have a physiologically tolerable pH. This is preferably achieved by buffers (buffer systems), which may themselves contribute to the total electrolyte content. The buffers are preferably bicarbonate, lactate or pyruvate.

Furthermore, dialysis solutions usually have a physiologically tolerable osmolarity. This is usually achieved by the electrolytes contained in the dialysis solution and inventive 6-deoxy-6-sulfanylcyclodextrins, which are physiologically tolerable as osmotically active compounds (osmotics) in the desired concentration.

The inventive dialysis solution preferably has an osmolarity in the range of 200 to 550 mosm/L.

In the case when the inventive dialysis solution is a hemodialysis solution, the osmolarity is preferably 200 to 350 mosm/L or 210 to 340 mosm/L, more preferably 220 to 330 mosm/L, even more preferably 230 to 320 mosm/L, most preferably 240 to 310 mosm/L and in particular 250 to 300 mosm/L. Methods for measuring the osmolarity and the osmotic pressure are familiar to the person skilled in the art. For example, these may be determined with the help of a membrane osmometer or other suitable measurement methods.

In the case when the inventive dialysis solution is a peritoneal dialysis solution, the osmolarity is preferably 200 to 570 mosm/L or 210 to 560 mosm/L, more preferably 220 to 550 mosm/L, even more preferably 230 to 540 mosm/L, most preferably 240 to 530 mosm/L and in particular 250 to 520 mosm/L. In a preferred embodiment, the osmolarity is 250±50 mosm/L or 250±45 mosm/L, more preferably 250±35 mosm/L, even more preferably 250±25 mosm/L, most preferably 250±15 mosm/L and in particular 250±10 mosm/L. In another preferred embodiment, the osmolarity is 300±50 mosm/L or 300±45 mosm/L, more preferably 300±35 mosm/L, even more preferably 300±25 mosm/L, most preferably 300±15 mosm/L and in particular 300±10 mosm/L. In another preferred embodiment, the osmolarity is 350±50 mosm/L or 350±45 mosm/L, more preferably 350±35 mosm/L, even more preferably 350±25 mosm/L, most preferably 350±15 mosm/L and in particular 300±10 mosm/L. In another preferred embodiment, the osmolarity is 400±50 mosm/L or 400±45 mosm/L, more preferably 400±35 mosm/L, even more preferably 400±25 mosm/L, most preferably 400±15 mosm/L and in particular 300±10 mosm/L. In another preferred embodiment, the osmolarity is 450±50 mosm/L or 450±45 mosm/L, more preferably 450±35 mosm/L, even more preferably 450±25 mosm/L, most preferably 450±15 mosm/L and in particular 450±10 mosm/L. In another preferred embodiment, the osmolarity is 500±50 mosm/L or 500±45 mosm/L, more preferably 500±35 mosm/L, even more preferably 500±25 mosm/L, most preferably 500±15 mosm/L and in particular 500±10 mosm/L.

The inventive dialysis solution preferably has a pH of 4.0 to 8.0, more preferably 4.2 to 7.5, even more preferably 4.4 to 6.8, most preferably 4.6 to 6.0 or 4.8 to 5.5 and in particular 5.0 to 5.2 or 5.0±0.1, measured at room temperature (20 to 23° C.). In a preferred embodiment, the pH is 4.8±1.0 or 4.8±0.8, more preferably 4.8±0.7 or 4.8±0.6, even more preferably 4.8±0.5 or 4.8±0.4, most preferably 4.8±0.3 or 4.8±0.2 and in particular 4.8±0.1. In another preferred embodiment, the pH is 5.0±1.0 or 5.0±0.8, more preferably 5.0±0.7 or 5.0±0.6, even more preferably 5.0±0.5 or 5.0±0.4, most preferably 5.0±0.3 or 5.0±0.2 and in particular 5.0±0.1. In another preferred embodiment, the pH is 5.2±1.0 or 5.2±0.8, more preferably 5.2±0.7 or 5.2±0.6, even more preferably 5.2±0.5 or 5.2±0.4, most preferably 5.2±0.3 or 5.2±0.2 and in particular 5.2±0.1. In another preferred embodiment, the pH is 5.5±1.0 or 5.5±0.8, more preferably 5.5±0.7 or 5.5±0.6, even more preferably 5.5±0.5 or 5.5±0.4, most preferably 5.5±0.3 or 5.5±0.2 and in particular 5.5±0.1. In another preferred embodiment, the pH is 6.0±1.0 or 6.0±0.8, more preferably 6.0±0.7 or 6.0±0.6, even more preferably 6.0±0.5 or 6.0±0.4, most preferably 6.0±0.3 or 6.0±0.2 and in particular 6.0±0.1. In another preferred embodiment, the pH is 6.5±1.0 or 6.5±0.8, more preferably 6.5±0.7 or 6.5±0.6, even more preferably 6.5±0.5 or 6.5±0.4, most preferably 6.5±0.3 or 6.5±0.2 and in particular 6.5±0.1. In another preferred embodiment, the pH is 7.0±1.0 or 7.0±0.8, more preferably 7.0±0.7 or 7.0±0.6, even more preferably 7.0±0.5 or 7.0±0.4, most preferably 7.0±0.3 or 7.0±0.2 and in particular 7.0±0.1. In another preferred embodiment, the pH is 7.4±1.0 or 7.4±0.8, more preferably 7.4±0.7 or 7.4±0.6, even more preferably 7.4±0.5 or 7.4±0.4, most preferably 7.4±0.3 or 7.4±0.2 and in particular 7.4±0.1. In another preferred embodiment, the pH is 8.0±1.0 or 8.0±0.8, more preferably 8.0±0.7 or 8.0±0.6, even more preferably 8.0±0.5 or 8.0±0.4, most preferably 8.0±0.3 or 8.0±0.2 and in particular 8.0±0.1.

The inventive dialysis solution contains one or more (for example, two, three, four or five) inventive 6-deoxy-6-sulfanylcyclodextrins, where the inventive 6-deoxy-6-sulfanylcyclodextrins are defined as given above.

The inventive dialysis solution contains the inventive 6-deoxy-6-sulfanylcyclodextrin in a total concentration of preferably 0.001 mM to 10 M or 0.01 to 1.0 M, more preferably 0.10 to 500 mM, even more preferably 1.0 to 250 mM, most preferably 10 to 100 mM and in particular 25 to 90 mM. In a preferred embodiment, the total concentration is 25±24 mM, more preferably 25±20 mM, even more preferably 25±15 mM, most preferably 25±10 mM and in particular 25±5 mM. In another preferred embodiment, the total concentration is 50±25 mM, more preferably 50±20 mM, even more preferably 50±15 mM, most preferably 50±10 mM and in particular 50±5 mM. In another preferred embodiment, the total concentration is 75±25 mM, more preferably 75±20 mM, even more preferably 75±15 mM, most preferably 75±10 mM and in particular 75±5 mM. In another preferred embodiment, the total concentration is 100±25 mM, more preferably 100±20 mM, even more preferably 100±15 mM, most preferably 100±10 mM and in particular 100±5 mM. In another preferred embodiment, the total concentration is 200±25 mM, more preferably 200±20 mM, even more preferably 200±15 mM, most preferably 200±10 mM and in particular 200±5 mM. The total concentration is preferably calculated by means of the average molecular weight of the inventive 6-deoxy-6-sulfanylcyclodextrins.

The inventive dialysis solution preferably contains the inventive 6-deoxy-6-sulfanylcyclodextrin in a total mass concentration of 0.01 g/L to 1.0 kg/L, more preferably 0.1 to 750 g/L, even more preferably 1.0 to 500 g/L, most preferably 10 to 250 g/L and in particular 100 to 200 g/L. In a preferred embodiment, the total mass concentration is 25±24 g/L, more preferably 25±20 g/L, even more preferably 25±15 g/L, most preferably 25±10 g/L and in particular 25±5 g/L. In another preferred embodiment, the total mass concentration is 50±25 g/L, more preferably 50±20 g/L, even more preferably 50±15 g/L, most preferably 50±10 g/L and in particular 50±5 g/L. In another preferred embodiment, the total mass concentration is 75±25 g/L, more preferably 75±20 g/L, even more preferably 75±15 g/L, most preferably 75±10 g/L and in particular 75±5 g/L. In another preferred embodiment, the total mass concentration is 100±25 g/L, more preferably 100±20 g/L, even more preferably 100±15 g/L, most preferably 100±10 g/L and in particular 100±5 g/L. In another preferred embodiment, the total mass concentration is 200±25 g/L, more preferably 200±20 g/L, even more preferably 200±15 g/L, most preferably 200±10 g/L and in particular 200±5 g/L.

The inventive dialysis solution may also contain other osmotically active substances such as glucose, polyglucose, crosslinked glucose or polyglucose, mannitol or glycerol.

The inventive dialysis solution preferably contains one or more electrolytes.

In the sense of the present invention, the term "electrolyte" stands for a substance containing free ions and having an electric conductivity. The electrolyte preferably dissociates completely into cations and anions without significantly altering the pH of an aqueous composition. This property differentiates electrolytes from buffer substances. The electrolytes are preferably present in a concentration, which results in essentially complete dissociation in water.

Preferred electrolytes are selected from the group of alkali metals, for example, $Na^+$ and $K^+$ and the alkaline earth metals, for example, $Ca^{2+}$ and $Mg^{2+}$. A preferred anion is $Cl^-$.

The inventive dialysis solution may contain additional anions, for example, bicarbonate, dihydrogen phosphate, hydrogen phosphate, phosphate, acetate, lactate and pyruvate. However, in the sense of the present invention, these anions (in suitable combinations with cations) are referred to not as electrolytes but instead as buffers, based on their buffering capacity.

In a preferred embodiment, the inventive dialysis solution contains $Na^+$ ions. The concentration of $Na^+$ ions is preferably 10 to 200 mM or 50 to 190 mM, more preferably 100 to 180 mM or 110 to 170 mM, even more preferably 115 to 165 mM or 120 to 160 mM, most preferably 125 to 155 mM and in particular 130 to 150 mM. In another preferred embodiment, the inventive dialysis solution does not contain any $Na^+$ ions.

In a preferred embodiment, the inventive dialysis solution contains $K^+$ ions. The concentration of $K^+$ ions is preferably 0.10 to 20 mM, more preferably 0.25 to 15 mM, even more preferably 0.50 to 10 mM, most preferably 0.75 to 7.5 mM and in particular 1.0 to 5.0 mM. In another preferred embodiment, the concentration of $K^+$ ions is 1.0±0.75, 2.0±0.75, 3.0±0.75, 4.0±0.75 or 5.0±0.75 mM and in particular 1.0±0.50, 2.0±0.50, 3.0±0.50, 4.0±0.50 or 5.0±0.50. In another preferred embodiment, the inventive dialysis solution does not contain any $K^+$ ions.

In a preferred embodiment, the inventive dialysis solution contains $Ca^{2+}$ ions. The concentration of $Ca^{2+}$ ions is preferably 0.1 to 3 mM, more preferably 0.25 to 2.75 mM, even more preferably 0.5 to 2.5 mM, most preferably 0.75 to 2.25 mM and in particular 1 to 2 mM. In another preferred embodiment, the concentration of $Ca^{2+}$ ions is 0.25, 0.5, 0.75, 1, 1.25, 1.5, 1.75 or 2 mM. In another preferred embodiment, the inventive dialysis solution does not contain any $Ca^{2+}$ ions.

In a preferred embodiment, the inventive dialysis solution contains $Mg^{2+}$ ions. The concentration of $Mg^{2+}$ ions is preferably 0.01 to 1 mM, more preferably 0.05 to 0.75 mM, even more preferably 0.1 to 0.5 mM, most preferably 0.15 to 0.4 mM and in particular 0.2 to 0.3 mM. In another preferred embodiment, the concentration of $Mg^{2+}$ ions is 0.05, 0.075, 0.1, 0.2, 0.25, 0.50 or 0.75 mM. In another preferred embodiment, the inventive dialysis solution does not contain any $Mg^{2+}$ ions.

In a preferred embodiment, the inventive dialysis solution concentration contains $Cl^-$ ions. The concentration of $Cl^-$ ions is preferably 10 to 300 mM, more preferably 25 to 250 mM, even more preferably 50 to 200 mM, most preferably 75 to 150 mM and in particular 80 to 125 mM. In another preferred embodiment, the concentration of $Cl^-$ ions is 100±50 mM, more preferably 100±25 mM, most preferably 100±10 mM and in particular 96±4 mM. In another preferred embodiment, the inventive dialysis solution does not contain any $Cl^-$ ions.

The inventive dialysis solution preferably contains one or more buffers.

The person skilled in the art will know of suitable buffers. Buffers usually include salts such as lactate, bicarbonate, carbonate, dihydrogen phosphate, hydrogen phosphate, phosphate, pyruvate, citrate, isocitrate, succinate, fumarate, acetate and lactate. The person skilled in the art will know that the corresponding cation of the aforementioned anions is part of the buffer, which is used to adjust the pH (for example, $Na^{\oplus}$ as a component of the buffer $NaHCO_3$). However, if the buffer salt has dissociated in water, it also acts as an electrolyte. For the purposes of this description, the concentrations of cations or anions and the total concentration of ions are calculated, regardless of whether they are used as components of electrolytes, buffers or other compounds (for example, as a salt of the inventive 6-deoxy-6-sulfanylcyclodextrins).

In a preferred embodiment, the buffer contains bicarbonate. Bicarbonate is a well-tolerated buffer system, which is in equilibrium with carbonate in an alkaline medium and in equilibrium with $H_2CO_3$ or $CO_2$ in an acidic medium. In addition to bicarbonate, other buffer systems may also be used if they have a buffering effect in the range of pH 4 to pH 8, more preferably in the range of pH 5 to pH 7.6 and in particular in the range of pH 7.6, 7.4, 7.2 and/or 7.0; for example, also including compounds such as lactate or pyruvate, which can be metabolized to bicarbonate in the body.

In another preferred embodiment, the buffer contains the salt of a weak acid, preferably lactate. The acid strength ($pK_s$) of the weak acid is preferably ≤55. The buffer may also be a mixture of substances having a buffing effect, e.g., a mixture containing bicarbonate and a salt of a weak acid (e.g., lactate). A low bicarbonate concentration has the advantage that the $CO_2$ pressure in the container is low.

In a preferred embodiment, the inventive dialysis solution is buffered with bicarbonate. The bicarbonate concentration is preferably 1.0 to 200 mM, more preferably 2.5 to 150 mM, even more preferably 5 to 100 mM, most preferably 5 to 75 mM or 10 to 50 mM and in particular 20 to 30 mM. In another preferred embodiment, the bicarbonate concentration 25 mM. In another preferred embodiment, the inventive dialysis solution does not contain any bicarbonate.

In a preferred embodiment, the inventive dialysis solution is buffered by lactate. The lactate concentration is preferably 1.0 to 200 mM, more preferably 2.5 to 150 mM, even more preferably 5 to 100 mM, most preferably 10 to 50 mM or 10 to 25 mM and in particular 15 mM. In another preferred embodiment, the inventive dialysis solution does not contain any lactate.

In a preferred embodiment, the inventive dialysis solution is buffered by acetate. The acetate concentration is preferably 1.0 to 100 mM, more preferably 1.0 to 50 mM, even more preferably 1.0 to 25 mM, most preferably 1.0 to 10 mM or 2.0 to 7.5 mM and in particular 2.5 to 7.0 mM. In another preferred embodiment, the inventive dialysis solution does not contain any acetate.

The total volume of dialysis solution is not limited. The volume usually amounts to several liters (suitable dosage volume for one patient) up to a few hundred liters (suitable storage volume for more than one patient).

As already explained above, the term "dialysis solution" in the sense of this invention is understood to be a ready-to-use dialysis solution, i.e., the dialysis solution may be used directly for dialysis therapy (hemodialysis or peritoneal dialysis).

In a preferred embodiment, the inventive dialysis solution is a peritoneal dialysis solution, as described below.

The peritoneal dialysis solution is biochemically adjusted so that it essentially corrects the metabolic acidosis associated renal insufficiency. The peritoneal dialysis solution preferably contains bicarbonate in approximately physiological concentrations. In a preferred embodiment, the peritoneal dialysis solution contains bicarbonate in a concentration of approximately 20 to 30 mM. In another preferred embodiment, the peritoneal dialysis solution contains a bicarbonate concentration of 25 mM.

Furthermore, the peritoneal dialysis solution preferably contains carbon dioxide with a partial pressure ($pCO_2$) of less than 60 mmHg. In a preferred embodiment, the $pCO_2$ of the peritoneal dialysis solution is essentially the same as the $pCO_2$ measured in blood vessels.

Furthermore, the peritoneal dialysis solution preferably has a pH of approximately 7.4. The peritoneal dialysis solution is therefore a physiologically tolerable solution.

The peritoneal dialysis solution preferably contains a weak acid with a $pK_s \leq 5$. The weak acids are preferably compounds that occur as physiological metabolites in the glucose metabolism. The weak acid is preferably selected from the group comprising lactate, pyruvate, citrate, isocitrate, ketoglutarate, succinate, fumarate, malate and oxaloacetate. These acids may be used alone or as a mixture in the peritoneal dialysis solution. The weak acids are preferably present in a concentration of 10 to 20 meq/L and essentially as sodium salts in the peritoneal dialysis solution. The weak acid is preferably present in the peritoneal dialysis solution in an amount corresponding to a daily metabolic hydrogen production of approximately 1 meq/kg/day.

The peritoneal dialysis solution contains at least one inventive 6-deoxy-6-sulfanylcyclodextrin as defined above.

The inventive peritoneal dialysis solution preferably contains a bicarbonate concentration and had a $pCO_2$ like that measured in healthy patients who are not renally insufficient. The weak acid diffuses from the dialysis solution into the blood of the dialysis patient along the concentration gradient and thus corrects the metabolic acidosis of the dialysis patient.

Another subject matter of this invention relates to multi-component systems for preparing the ready-to-use dialysis solutions described above. They are preferably prepared in a manner that is described in detail, i.e., by following appropriate instructions (protocol). This preparation may take place manually, e.g., by mixing individual components or by diluting one component with water. However, the preparation may also be automated, for example, by means of a device which is suitable for these processes and may be available commercially. The preparation need not necessarily lead to a dialysis solution having a static composition (always uniform) but instead may also lead to a dialysis solution which undergoes continuous changes in composition, where these changes are monitored by a suitable device. For example, the inventive 6-deoxy-6-sulfanylcyclodextrin may be present in a dialysis solution which is diluted continuously during dialysis therapy, so that the patient is exposed to a decreasing concentration of 6-deoxy-6-sulfanylcyclodextrin.

In a preferred embodiment, the inventive dialysis solutions are suitable for use in treatment of renal insufficiency.

In another preferred embodiment, the inventive dialysis solutions are suitable for use in dialysis therapy.

In another preferred embodiment, the inventive dialysis solutions are suitable for use in hemodialysis and/or peritoneal dialysis therapy.

Another subject matter of this invention relates to a kit, which is configured for preparation of the inventive dialysis solutions, where the kit comprises:
 a first component,
 a second component and
 optionally one or more additional components, and
the inventive dialysis solution is prepared by mixing the first component with the second component and optionally the additional component(s).

The kit comprises at least one first component and one second component. The kit may also comprise additional components, e.g., a third component and a fourth component. The kit preferably consists of two components, which are preferably different from one another.

In the sense of the present invention, the term "component" comprises liquid, semisolid or solid compositions, which may be the same as or different from one another, such that the inventive ready-to-use dialysis solution is obtained by mixing all the components of the kit. A single component preferably contains a portion of the ingredients, which are present in the ready-to-use dialysis solution.

The first and second components may, independently of one another, be solid, semisolid or liquid. In the case when the components are liquid, they may be solutions or dispersions (e.g., dispersions or suspensions).

In a preferred embodiment, the first component is liquid, preferably pure water or an aqueous solution, and the second component is also liquid. In another preferred embodiment, the first component is liquid, preferably pure water or an aqueous solution, and the second component is solid, preferably a powdered mixture.

The first component is preferably a solution containing osmotically active substances (for example, inventive 6-deoxy-6-sulfanylcyclodextrin), calcium ions, magnesium ions, hydronium ions and chloride ions.

The inventive kit may have various embodiments. For example, the individual components may be in separate containers (for example, individual bags). However, the inventive kit is preferably a container, for example, a multichamber container system (for example, a flexible or rigid multichamber container system), preferably a flexible multichamber bag system.

The inventive kit is preferably a multichamber container system containing the first component, the second component and optionally one or more additional components chambers, which are separated from one another by soluble or breakable separation systems (for example, breakable separating parts), where the first component, the second component and optionally one or more additional components may be mixed together after dissolving or breaking the separation system in order to obtain the inventive dialysis solution.

The multichamber container may also be in the form of a plastic container (for example, multichamber plastic bags), each of which contains a separate chamber for each individual component. The plastic container preferably contains the individual component solutions in chambers which are separated from one another by separating elements.

The multichamber container is preferably a two-chamber bag comprising a plastic container having a first chamber and a second chamber, where the chambers are separated from one another by a soluble or breakable separation system, and the first chamber contains the first component and the second chamber contains the second component. Dissolving or breaking the separation system causes the two components to be mixed, resulting in the ready-to-use dialysis solution. The first chamber and the second chamber are preferably arranged adjacent to one another in the container and are separated from one another by the separation system. The separation system is preferably a separating seam (for example, soluble or breakable weld). The separating seam is preferably opened by applying pressure to one of the chambers, where the separating seam breaks and/or dissolves and the contents of the two chambers are mixed, and the mixture may be used as the ready-to-use dialysis solution in dialysis therapy.

The first component of the inventive kit is preferably a sterile solution containing an acid and having a pH≤6.0. The second component is preferably also a sterile solution, preferably containing a buffer and having a pH≥7.0.

The inventive 6-deoxy-6-sulfanylcyclodextrin may be contained in the first component or in the second component as well as in both components in the same or different concentrations. In a preferred embodiment, the inventive 6-deoxy-6-sulfanylcyclodextrin is present only in the first (acidic) component. In another preferred embodiment, the inventive 6-deoxy-6-sulfanylcyclodextrin is present only in the second (basic) component. The first component and/or the second component and/or the optional additional component(s) may contain one or more electrolytes as well as buffers.

The person skilled in the art will recognize that mixing of the individual components usually entails a dilution effect for the case when the components contain the ingredients in different concentrations. For example, if the inventive 6-deoxy-6-sulfanylcyclodextrin is present exclusively in one of the components, mixing of these components with at least one other component leads to an increase in the volume with respect to the available quantity of inventive 6-deoxy-6-sulfanylcyclodextrin and thus leads to a dilution, i.e., a reduction in the 6-deoxy-6-sulfanylcyclodextrin concentration. Consequently the component preferably contains the inventive 6-deoxy-6-sulfanylcyclodextrin in a higher concentration than the ready-to-use dialysis solution.

The concentration of inventive 6-deoxy-6-sulfanylcyclodextrin in the component is preferably close to the saturation concentration at a temperature of 5° C. in order to ensure an adequate stability in storage at higher temperatures.

In a preferred embodiment, the total concentration by weight of inventive 6-deoxy-6-sulfanylcyclodextrin in the component is 0.01 g/L to 1.0 kg/L, more preferably 0.1 to 750 g/L, even more preferably 1.0 to 500 g/L, most preferably 10 to 250 g/L and in particular 100 to 200 g/L. In another preferred embodiment, the total concentration by weight of inventive 6-deoxy-6-sulfanylcyclodextrin in the component is 25±24 g/L, more preferably 25±20 g/L, even more preferably 25±15 g/L, most preferably 25±10 g/L and in particular 25±5 g/L. In another preferred embodiment, the total concentration by weight of inventive 6-deoxy-6-sulfanylcyclodextrin in the component is 50±25 g/L, more preferably 50±20 g/L, even more preferably 50±15 g/L, most preferably 50±10 g/L and in particular 50±5 g/L. In another preferred embodiment, the total mass concentration by weight of inventive 6-deoxy-6-sulfanylcyclodextrin in the component is 75±25 g/L, more preferably 75±20 g/L, even more preferably 75±15 g/L, most preferably 75±10 g/L and in particular 75±5 g/L. In another preferred embodiment, the total concentration by weight of inventive 6-deoxy-6-sulfanylcyclodextrin in the component is 100±25 g/L, more preferably 100±20 g/L, even more preferably 100±15 g/L, most preferably 100±10 g/L and in particular 100±5 g/L. In another preferred embodiment, the total concentration of inventive 6-deoxy-6-sulfanylcyclodextrin in the component is 200±25 g/L, more preferably 200±20 g/L, even more preferably 200±15 g/L, most preferably 200±10 g/L and in particular 200±5 g/L.

In a preferred embodiment, the second component contains the total amount of inventive 6-deoxy-6-sulfanylcyclodextrin and a suitable buffer, which adjusts the pH of the second component to more than 7.0, preferably to more than 7.5, more preferably to more than 8.0, most preferably to more than 8.5 and in particular to more than 9.0. This may preferably be achieved by using a bicarbonate, which may be present in the form of dissociated sodium bicarbonate and or potassium bicarbonate, for example. In another preferred embodiment, the second component is solid and comprises a powdered mixture containing at least one inventive 6-deoxy-6-sulfanylcyclodextrin and at least one buffer, for example, sodium bicarbonate and/or potassium bicarbonate.

The multichamber bag is preferably suitable for preparing a dialysis solution suitable for use in peritoneal dialysis therapy and preferably containing the following ingredients in the following concentrations:

$Ca^{2\oplus}$ 0.5 to 5 meq/L;
$Mg^{2\oplus}$ 0 to 3.0 meq/L;
$Cl^{\ominus}$ 90.5 to 121 meq/L;
$K^{\oplus}$ 0 to 4.0 meq/L;
$HCO_3^{\ominus}$ 25 to 40 meq/L; where one chamber of the multichamber bag system contains a first acidic concentrate and another chamber contains a second basic concentrate, where the acidic concentrate contains $Ca^{2\oplus}$ ions and the basic concentrate contains $HCO_3^{\ominus}$ ions but does not contain any $Ca^{2\oplus}$ ions; and after dissolving or breaking the separation system (for example, a separation seam), the two concentrates can be mixed with one another, such that the mixing of the two concentrates leads to preparation of the ready-to-use dialysis solution, and the pH of the ready-to-use dialysis solution is 7.0 to 7.6.

The basic concentrate preferably contains at least one inventive 6-deoxy-6-sulfanylcyclodextrin and optionally glucose and/or polyglucose, whereas the acidic concentrate does not contain any inventive 6-deoxy-6-sulfanylcyclodextrin or any glucose and/or polyglucose.

The basic concentrate preferably contains an amount of bicarbonate which leads to a bicarbonate concentration of the ready-to-use dialysis solution of at least 20 mM. The bicarbonate concentration the basic component is preferably so high that the ready-to-use dialysis solution has a bicarbonate concentration of 25 mM.

The pH of the basic buffered second concentrate is preferably adjusted with hydrochloric acid.

The two concentrates are preferably mixed with one another in a volume ratio of 10:1 to 1:10 or 8:1 to 1:8, more preferably 5:1 to 1:5 or 3:1 to 1:3, even more preferably 2:1 to 1:2 and in particular 1:1.

The multichamber bag preferably has a gas barrier film which prevents gaseous $CO_2$ from escaping out of the system. The person skilled in the art will be familiar with gas barrier films.

A preferred subject matter of this invention relates to a method for preparing a dialysis solution, in which the desired mixing ratio is automatically achieved by a dialysis machine or a peritoneal dialysis cycler.

In a preferred embodiment, the invention relates to a solid composition, which is suitable for preparing the inventive dialysis solution by dissolving in a defined volume of a solvent (for example, water). The solid composition is preferably a component as described above and is thus a constituent of the inventive kit.

The solid composition contains the inventive 6-deoxy-6-sulfanylcyclodextrin in any solid form, for example, as a powder, granules, pellets, etc. The inventive 6-deoxy-6-sulfanylcyclodextrin may be in the form of a lyophilisate or may be spray-dried.

The inventive solid composition preferably contains a bicarbonate salt, such as, for example, sodium bicarbonate or potassium bicarbonate. The substance quantity ratio of bicarbonate to the inventive 6-deoxy-6-sulfanylcyclodextrin in the solid composition is preferably 1:100 to 100:1, more preferably 1:50 to 50:1, even more preferably 1:25 to 25:1, most preferably 1:10 to 10:1 and in particular 1:5 to 5:1.

The defined volume of solvent needed to prepare the inventive dialysis solution by dissolving the solid composition is preferably 1.0 to 2000 liters. The solvent is preferably purified water, sterilized water or water for injection purposes, which may optionally contain one or more of the electrolytes described above, one or more osmotically active substances (for example, at least one inventive 6-deoxy-6-sulfanylcyclodextrin) and/or one or more of the buffers described above.

Another subject matter of this invention relates to the use of at least one inventive 6-deoxy-6-sulfanylcyclodextrin for preparing the inventive dialysis solution (hemodialysis solution or peritoneal dialysis solution).

Another subject matter of this invention relates to the use of an inventive kit for preparing the inventive dialysis solution (hemodialysis solution or peritoneal dialysis solution).

Another subject matter of this invention relates to the use of an inventive solid composition for preparing the inventive dialysis solution (hemodialysis solution or peritoneal dialysis solution).

EXAMPLES

The compounds in Examples 1 to 4 were prepared according to a published procedure (Steffen et al., Chem. Eur. J. 2007. 13, 6801-6809).

A batch of each individual exemplary compound was prepared with a low degree of substitution of approximately 2 to 3, and a batch with a high degree of substitution of approximately 6 to 7 was also prepared.

Example 1

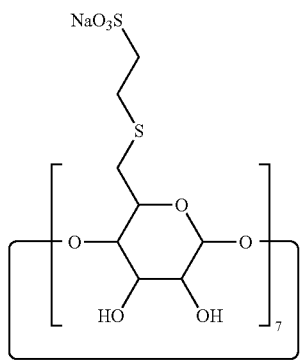

Example 2

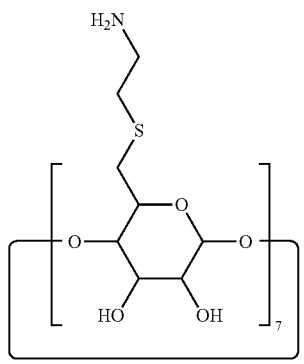

Example 3

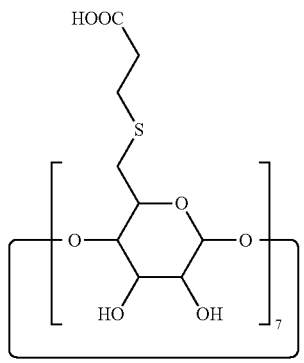

Example 4

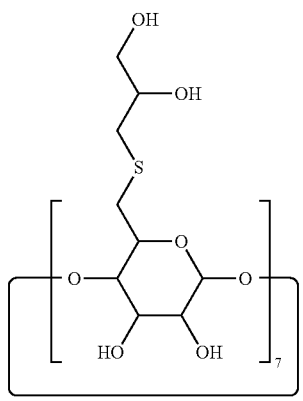

Example 5

In a comparative experiment, a filling volume of 10 mL of an osmotic agent in a concentration of 5% (m/m) in a test solution containing 1 mmol/L $Ca^{2+}$, 0.5 mmol/L $Mg^{2+}$, 138 mmol/L $Na^+$, 106 mmol/L $Cl^-$ and 35 mmol/L lactate in a semi-permeable tubing (regenerated cellulose, MWCO: 1000, Roth) filled and stored at a temperature of 38° C. in a bath of the same test solution for 24 hours with agitation. At various times the volume increase of the filling volume of the tubing was determined, which reflects the osmotic effect of the agent. As osmotic agents were used a cyclodextrin derivative according to the present invention as well as the established osmotic agents glucose and icodextrin.

The cyclodextrin derivative used in the experiment has the following structural formula:

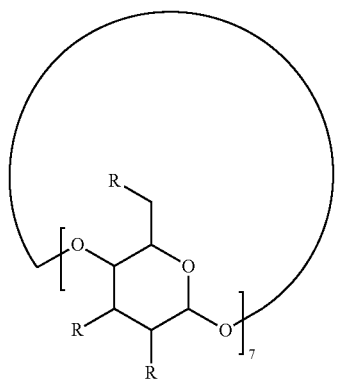

R=OH or S—CH2-CH2-COONa

The results are shown in the FIG. 1 as a diagram.

The cyclodextrin derivative shows a greater osmotic effect than glucose and icodextrin.

Comparative Examples

The exemplary compounds 1 through 4 were compared with the equivalent β-cyclodextrin derivatives.

The exemplary compounds had a lower number of positional isomers and compounds of different molecular weights (determined analytically by means of HPLC or LC/MS/MS, for example) in comparison with the equivalent cyclodextrin compounds.

In comparison with the cyclodextrin derivatives according to U.S. Pat. No. 4,889,634 and JP 8071146, the exemplary compounds 1 through 4 have a higher colloid osmotic pressure and thus have a greater osmotic efficacy.

The invention claimed is:

1. A dialysis solution comprising
   (i) at least one 6-deoxy-6-sulfanylcyclodextrin of the general structure I:

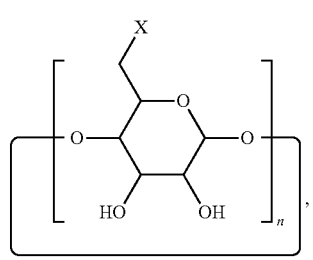

where
   a) X stands for S—R or —OH, wherein S—R is present at a degree of substitution ≥0.0001 and ≤n
   b) n stands for 6, 7 or 8,
   c) R is selected from the group consisting of $C_{1-6}$-alkyl-$NR^1R^2$, $C_{1-6}$-alkyl-$N^+R^3R^4R^5$, $C_{1-6}$-alkyl-COOH, $C(=O)C_{1-6}$-alkyl-COOH, —C(=O)—$CH_2$—C(OH)(COOH)—$CH_2$—COOH, dihydroxylated $C_{1-6}$-alkyl, $C_{1-6}$-alkyl-$PO_3H_2$ and —$C_{1-6}$-alkyl-$SO_3H$, where $R^1$, $R^2$, $R^3$, $R^4$ and $R^5$, independently of one another, stand for H or —$C_{1-3}$-alkyl, and
   (ii) the following ingredients in the following concentrations:
   $Ca^{2\oplus}$ 0.5 to 5 meq/L;
   $Mg^{2\oplus}$ 0 to 3.0 meq/L;
   $Cl^\ominus$ 90.5 to 121 meq/L;
   $K^\oplus$ 0 to 4.0 meq/L;
   $HCO_3^\ominus$ 25 to 40 meq/L.

2. The dialysis solution according to claim 1, wherein the degree of substitution of the 6-deoxy-6-sulfanylcyclodextrin is ≥1 and ≤n.

3. The dialysis solution according to claim 1, wherein the degree of substitution of the 6-deoxy-6-sulfanylcyclodextrin is ≥n−1 and ≤n.

4. The dialysis solution according to claim 1, wherein a 7.5 wt % aqueous solution of 6-deoxy-6-sulfanylcyclodextrin has an osmolarity of ≥5 mosm/L.

5. A process for preparing a dialysis solution according to claim 1, the process comprising mixing the at least one 6-deoxy-6-sulfanylcyclodextrin compound with the other components of the dialysis solution as recited in claim 1.

* * * * *